United States Patent
Zhao et al.

(10) Patent No.: US 11,618,738 B2
(45) Date of Patent: Apr. 4, 2023

(54) COMPOUND AND APPLICATION THEREOF IN TREATING INFLAMMATION OR INFLAMMATION-RELATED DISEASES

(71) Applicant: SICHUAN CENTER FOR TRANSLATIONAL MEDICINE OF TRADITIONAL CHINESE MEDICINE, Sichuan (CN)

(72) Inventors: Junning Zhao, Sichuan (CN); Jiajiu Shaw, Sichuan (CN); Yiguan Zhang, Sichuan (CN); Zhujun Yin, Sichuan (CN)

(73) Assignee: SICHUAN CENTER FOR TRANSLATIONAL MEDICINE OF TRADITIONAL CHINESE MEDICINE, Sichuan (CN)

( * ) Notice: Subject to any disclaimer, the term of this patent is extended or adjusted under 35 U.S.C. 154(b) by 249 days.

(21) Appl. No.: 16/757,796

(22) PCT Filed: Aug. 14, 2018

(86) PCT No.: PCT/CN2018/100503
§ 371 (c)(1),
(2) Date: Apr. 21, 2020

(87) PCT Pub. No.: WO2019/034059
PCT Pub. Date: Feb. 21, 2019

(65) Prior Publication Data
US 2021/0355093 A1 Nov. 18, 2021

(30) Foreign Application Priority Data
Aug. 14, 2017 (CN) .......................... 201710692801.2

(51) Int. Cl.
C07D 261/18 (2006.01)
A61P 19/06 (2006.01)
A61P 19/02 (2006.01)
A61P 29/00 (2006.01)

(52) U.S. Cl.
CPC ............ *C07D 261/18* (2013.01); *A61P 19/02* (2018.01); *A61P 19/06* (2018.01); *A61P 29/00* (2018.01)

(58) Field of Classification Search
CPC ........ C07D 261/18; A61P 19/06; A61P 19/02; A61P 29/00
See application file for complete search history.

(56) References Cited

U.S. PATENT DOCUMENTS

| 6,727,272 B1 * | 4/2004 | Lee ...................... C07D 261/18 514/378 |
| 7,291,743 B2 * | 11/2007 | Shaw ................... C07D 261/18 548/248 |
| 2006/0223873 A1 | 10/2006 | Shaw et al. |

FOREIGN PATENT DOCUMENTS

| CN | 101883760 A | 11/2010 |
| JP | 2016030727 A | 3/2016 |
| WO | 2009010454 A2 | 1/2009 |

OTHER PUBLICATIONS

Lepage et al., 27(6) Euro. J. Med. Chem. 581-93 (1992) (Year: 1992).*
International Search Report (in English and Chinese) and Written Opinion issued in PCT/CN2018/100503, dated Nov. 5, 2018, 12 pages provided.
Lepage et al., "New N-Aryl Isoxazolecarboxamides and N-Isoxazolylbenzamides as Anticonvulsant Agents", European Journal of Medicinal Chemistry, vol. 27, Issue 6, Dec. 31, 1992, pp. 591-593; cited in International Search Report.
International Preliminary Report on Patentability (with English translation) issued in PCT/CN2018/100503, dated Feb. 18, 2020, 4 pages provided.

* cited by examiner

*Primary Examiner* — Timothy R Rozof
(74) *Attorney, Agent, or Firm* — Hamre, Schumann, Mueller & Larson, P.C.

(57) ABSTRACT

The present invention relates to a compound and the application thereof in treating inflammation or inflammation-related diseases, and more specifically to a compound UTLOH combination. Said compound effectively inhibits the level of LPS-induced PGE2 and NO, while effectively treating inflammatory or inflammatory-related diseases.

10 Claims, 2 Drawing Sheets

COMPOUND AND APPLICATION THEREOF IN TREATING INFLAMMATION OR INFLAMMATION-RELATED DISEASES

TECHNICAL FIELD

The present invention relates to the field of medicinal chemistry, in particular, to a new compound and an application thereof in the treatment of inflammation-related diseases.

BACKGROUND

Inflammation is the immune system's response to infection and injury. The pathogenesis of many diseases or health problems involves inflammation. These include rheumatoid arthritis, osteoarthritis, psoriatic arthritis, reactive arthritis, ankylosing spondylitis, gouty arthritis, fever, mild to moderate pain caused by inflammation and tissue damage, lumbago, inflammation on elbow, headache, migraine, acute gout, menstrual pain, metastatic bone pain, postoperation pain, muscle guarding, pain caused by Parkinson's disease and macular edema. Many anti-inflammatory drugs are currently available; a specific example is leflunomide.

Leflunomide is an anti-inflammatory agent; it is approved for the treatment of rheumatoid arthritis and inflammation-related diseases in Europe and the United States. However, it is associated with many adverse reactions.

Therefore, there is an urgent need in the art to develop a new compound that can treat inflammation or related diseases thereof with a good curative effect, small side effect, and simple synthetic method.

SUMMARY OF THE INVENTION

The object of the present invention is to provide a new compound which can treat inflammation or related diseases thereof with a good curative effect, small side effect and simple synthesis method.

In a first aspect of the present invention, it provides a compound of Formula I, or a salt thereof, or an optical isomer thereof, or a raceme thereof, or a solvate thereof, or a precursor thereof,

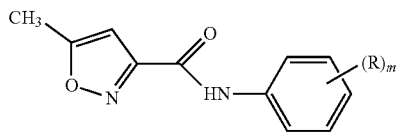
(I)

wherein each R is independently selected from the group consisting of —OH, —OCH$_3$, —OCH$_2$CH$_3$;

m is an integer of 1, or 2 or 3.

In another preferred embodiment, when R is —OCH$_3$ or —OCH$_2$CH$_3$, m is 1.

In another preferred embodiment, when R is —OCH$_3$, m is 2.

In another preferred embodiment, each R may be the same or different.

In another preferred embodiment, R is independently selected from the group consisting of —OH.

In another preferred embodiment, R includes at least 2 hydroxyl groups.

In another preferred embodiment, m further includes an integer of 4 or 5.

In another preferred embodiment, when R is —OCH$_3$, m further includes 4 or 5.

In another preferred embodiment, m is 2.

In another preferred embodiment, the compound is selected from the group consisting of

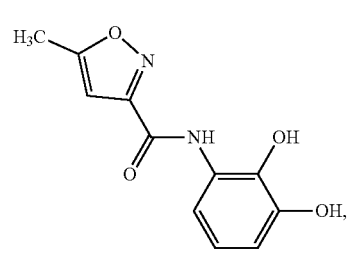
(UTLOH-4d)

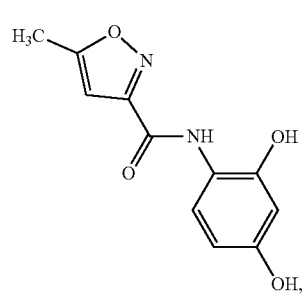
(UTLOH-4e)

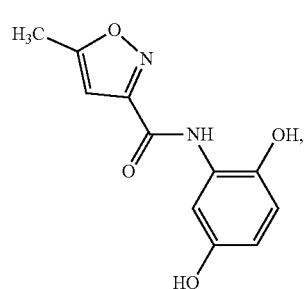
(UTLOH-4f)

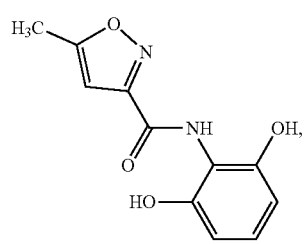
(UTLOH-4g)

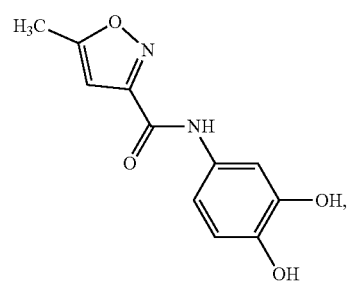
(UTLOH-4h)

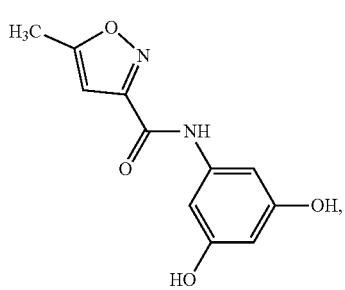
(UTLOH-4i)

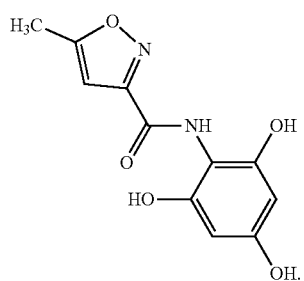
(UTLOH-4k)

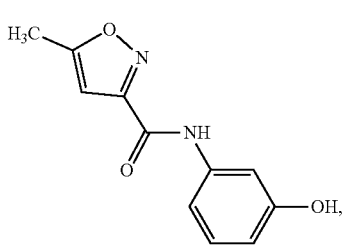
(UTLOH-4b)

and

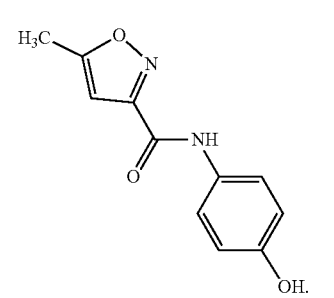
(UTLOH-4c)

In a second aspect of the present invention, it provides a pharmaceutical composition, comprising
(i) the compound of Formula I, or a salt thereof, or an optical isomer thereof, or a raceme thereof, or a solvate thereof, or a precursor thereof according to the first aspect of the present invention; and
(ii) a pharmaceutically acceptable carrier;
wherein the definition of the compound of Formula I is as described in the first aspect of the present invention.

In another preferred embodiment, the pharmaceutical composition contains 0.0001-99 wt % (preferably 0.01-90 wt %, more preferably 0.1-80 wt %) of the component (i), based on the total weight of the pharmaceutical composition.

In a third aspect of the present invention, it provides a pharmaceutical composition, including:
(i) a first active ingredient, the first active ingredient is a compound of formula II,

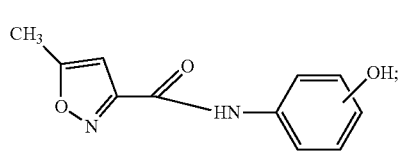
(II)

and
(ii) a pharmaceutically acceptable carrier.

In another preferred embodiment, the compound of Formula II is selected from the group consisting of

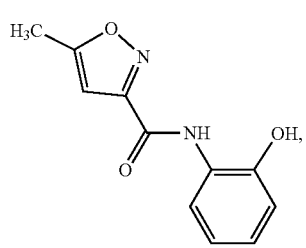
(UTLOH-4a)

In another preferred embodiment, the pharmaceutical composition contains 0.0001-99 wt % (preferably 0.01-90 wt %, more preferably 0.1-80 wt %) of component (i), based on the total weight of the pharmaceutical composition.

In another preferred embodiment, the pharmaceutical composition further comprises a second active ingredient, which is the compound of Formula I according to the first aspect of the present invention, or a salt thereof, or an optical isomer thereof, or a raceme thereof, or a solvate thereof, or a precursor thereof; wherein the definition of the compound of Formula I is as described in the first aspect of the present invention.

In another preferred embodiment, the weight ratio of the first active ingredient and the second active ingredient is 1:100 to 100:1, preferably 1:10 to 10:1.

In another preferred embodiment, the pharmaceutical composition contains 0.0001-99 wt % (preferably 0.01-90 wt %, more preferably 0.1-80 wt %) of component (i), based on the total weight of the pharmaceutical composition.

In another preferred embodiment, the pharmaceutical composition contains 0.0001-99 wt % (preferably 0.01-90 wt %, more preferably 0.1-80 wt %) of the second active ingredient, based on the total weight of the pharmaceutical composition.

In another preferred embodiment, the pharmaceutical composition can be a single compound or a mixture of multiple compounds.

In another preferred embodiment, the pharmaceutical composition is used to prepare a medicament or a preparation for treating an inflammation or inflammation-related disease.

In another preferred embodiment, the pharmaceutical composition is used to prepare a medicament or a preparation for treating a gout or gout-related disease.

In another preferred embodiment, the pharmaceutical composition is used to prepare a medicament or a preparation for an analgesia or analgesia-related disease.

In another preferred embodiment, the gout or gout-related disease is selected from the group consisting of acute characteristic arthritis, chronic tophi disease, acute onset arthritis, tophi formation, tophi chronic arthritis, urate nephropathy, uric acid urinary tract calculi, and a combination thereof.

In another preferred embodiment, the gout refers to acute characteristic arthritis and chronic tophi disease.

In another preferred embodiment, the gout includes acute onset arthritis, tophi formation, tophi chronic arthritis, urate nephropathy and uric acid urinary tract calculi.

In another preferred embodiment, the analgesia refers to the treatment of acute and chronic pain.

In another preferred embodiment, the analgesia refers to the treatment of acute pain, including: acute injury pain in soft tissue and joint, pain after surgery, obstetric pain, acute herpes zoster pain, and/or gout.

In another preferred embodiment, the analgesia refers to the treatment of chronic pain, including: soft tissue and joint strain or degenerative pain, discgenic pain disease, and/or neurogenic pain.

In another preferred embodiment, the analgesia refers to the treatment of intractable pain, including: trigeminal neuralgia, postherpetic neuralgia, and/or intervertebral disc herniation.

In another preferred embodiment, the analgesia refers to the treatment of cancer pain, including: advanced tumor pain and/or tumor metastasis pain.

In another preferred embodiment, the analgesia refers to the treatment of special pain types, including: thromboangiitis, intractable angina pectoris and/or idiopathic chest pain.

In another preferred embodiment, the pharmaceutical composition is used to prepare a selective regulator of LPS-induced PGE2 and NO.

In another preferred embodiment, the inflammation or inflammation-related disease is selected from the group consisting of rheumatoid arthritis, osteoarthritis, psoriatic arthritis, reactive arthritis, ankylosing spondylitis, gouty arthritis, fever, mild to moderate pain caused by inflammation and tissue damage, lumbago, inflammation of the elbow, headache, migraine, acute gout, menstrual pain, metastatic bone pain, postoperation pain, muscle guarding, pain caused by Parkinson's disease and macular edema, and a combination thereof.

In another preferred embodiment, the pharmaceutical composition further includes an additional medicament for treating an inflammation or inflammation-related disease.

In another preferred embodiment, the additional medicament for treating the inflammation or inflammation-related disease is selected from the group consisting of dexamethasone, ibuprofen, leflunomide, teriflunomide, malononitrilamide, diclofenac sodium, diclofenac potassium, naproxen, naproxen sodium, and a combination thereof.

In a fourth aspect of the present invention, it provides a use of a compound of Formula I, or a salt thereof, or an optical isomer, or a raceme thereof, or a solvate thereof, or a precursor thereof according to the first aspect of the present invention, a pharmaceutical composition according to the second aspect of the present invention or the third aspect of the present invention for the manufacturing of a medicament or a preparation for (i) treating an inflammation or inflammation-related disease; and/or (ii) regulating the levels of PGE2 and NO induced by LPS.

In another preferred embodiment, the medicament or preparation is also used for (iii) the treatment of gout; and/or (iv) analgesia.

In another preferred embodiment, the regulation of the levels of PGE2 and NO induced by LPS is the inhibition of the levels of PGE2 and NO.

In another preferred embodiment, the inflammation or inflammation-related disease is selected from the group consisting of rheumatoid arthritis, osteoarthritis, psoriatic arthritis, reactive arthritis, ankylosing spondylitis, gouty arthritis, fever, mild to moderate pain caused by inflammation and tissue damage, lumbago, inflammation of the elbow, headache, migraine, acute gout, menstrual pain, metastatic bone pain, postoperation pain, muscle guarding, pain caused by Parkinson's disease and macular edema, and a combination thereof.

In another preferred embodiment, the gout includes acute characteristic arthritis and/or chronic tophi disease.

In another preferred embodiment, the gout includes acute onset arthritis, tophi formation, tophi chronic arthritis, urate nephropathy, and/or uric acid urinary tract calculi.

In another preferred embodiment, the analgesia refers to the treatment of acute and chronic pain.

In another preferred embodiment, the analgesia refers to the treatment of acute pain, including: acute injury pain in soft tissue and joint, postoperative pain, obstetric pain, acute herpes zoster pain, and/or gout.

In another preferred embodiment, the analgesia refers to the treatment of chronic pain, including: soft tissue and joint strain or degenerative pain, discgenic pain disease, and/or neurogenic pain.

In another preferred embodiment, the analgesia refers to the treatment of intractable pain, including: trigeminal neuralgia, postherpetic neuralgia, and/or intervertebral disc herniation.

In another preferred embodiment, the analgesia refers to the treatment of cancer pain, including: advanced tumor pain and/or tumor metastasis pain.

In another preferred embodiment, the analgesia refers to the treatment of special pain types, including: thromboangiitis, intractable angina pectoris, and/or idiopathic chest pain.

In a fifth aspect of the present invention, it provides a method for preparing a compound of Formula I or a salt thereof, comprising the steps:

(a) reacting compound I-2 with compound I-A1 in an inert solvent, thereby forming a compound of Formula I;

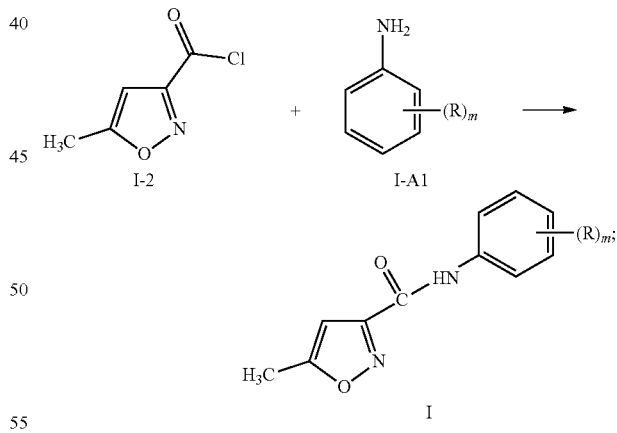

in the above formulas, R and m are defined as described in the first aspect of the present invention.

In another preferred embodiment, the inert solvent is selected from the group consisting of dichloromethane (DCM), chloroform, benzene, and a combination thereof.

In another preferred embodiment, the reaction is carried out in the presence of an acid binding agent.

In another preferred embodiment, the acid binding agent is selected from the group consisting of potassium carbonate ($K_2CO_3$), triethylamine ($Et_3N$), pyridine (Py), and a combination thereof.

In another preferred embodiment, in step (a), the reaction temperature is 0-150° C. (or reflux temperature), preferably, 10-80° C., more preferably, 20-60° C.

In another preferred embodiment, in step (a), the reaction time is 0.1-12 hours, more preferably, 0.2-5 hours, more preferably, 0.4-3 hours.

In another preferred embodiment, in Formula I-A1, R is methoxyl.

In another preferred embodiment, the compound of Formula I-2 is prepared by the following method:

(i) reacting compound I-1 with $SOCl_2$ in an inert solvent, thereby forming compound 1-2;

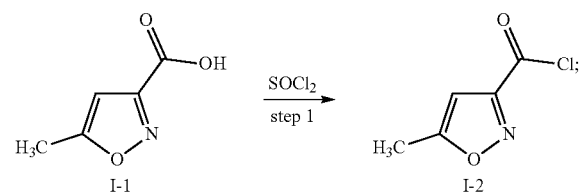

In another preferred embodiment, the inert solvent is selected from the group consisting of dichloromethane (DCM), chloroform, benzene, and a combination thereof.

In another preferred embodiment, in step (a), the reaction temperature is 0-150° C. (or reflux temperature), preferably, 10-80° C., more preferably, 20-60° C.

In another preferred embodiment, in step (a), the reaction time is 0.1-12 hours, more preferably, 0.2-5 hours, more preferably, 0.4-3 hours.

In another preferred embodiment, the method further includes a demethylation step.

In another preferred embodiment, the demethylation is carried out in the presence of an inert solvent.

In another preferred embodiment, the inert solvent is selected from the group consisting of dichloromethane, chloroform, benzene, and a combination thereof.

In a sixth aspect of the present invention, it provides an in vitro method for inhibiting PGE2 and NO induced by LPS, comprising the steps:

in the presence of LPS, contacting the compound of Formula I or the compound of Formula II or the pharmaceutical composition according to the second aspect of the present with a mammalian cell, so that the compound of Formula I or the compound of Formula II inhibits the levels of PGE2 and NO induced by LPS, wherein the compound of Formula I is defined as described in the first aspect of the present invention, the compound of Formula II is

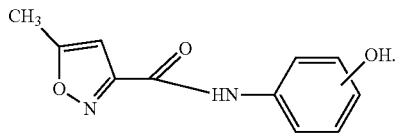

In another preferred embodiment, the compound of Formula II is selected from the group consisting of

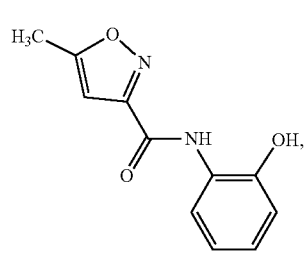

(UTLOH-4a)

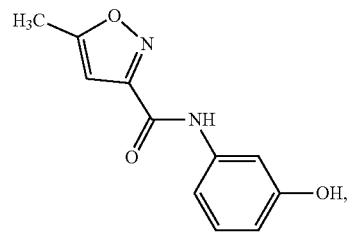

(UTLOH-4b)

and

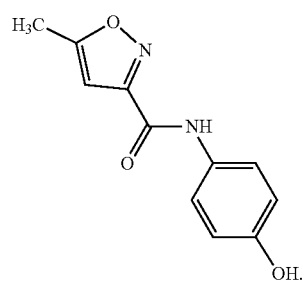

(UTLOH-4c)

In another preferred embodiment, the mammalian cell comprises a human or non-human mammalian cell.

In another preferred embodiment, the non-human mammal comprises a rodent (such as a mouse, rat, rabbit), and a primate (such as a monkey).

In another preferred embodiment, the cell comprises a RAW 264.7 cell.

In another preferred embodiment, the method is non-therapeutic and non-diagnostic.

In a seventh aspect of the present invention, it provides a method for treating an inflammation or inflammation-related disease, comprising:

administering the compound of Formula I according to the first aspect of the present invention or the pharmaceutical composition according to the second aspect of the present invention or the third aspect of the present invention to a subject in need.

In another preferred embodiment, the subject includes a human or non-human mammal.

In another preferred embodiment, the non-human mammal includes a rodent (such as a mouse, rat, rabbit), and a primate (such as a monkey).

In another preferred embodiment, the administration dosage is 0.01-1000 mg/kg/day, preferably 0.1-100 mg/kg/day, more preferably 1-50 mg/kg/day.

In another preferred embodiment, the frequency of administration is 1-3 times/day, preferably, 1-2 times/day.

In another preferred embodiment, the frequency of administration is about 0.001 to about 1000 mg/kg body weight per day, preferably, about 1.0 to about 30 mg/kg body weight per day.

In another preferred embodiment, the administration includes one or more cycles, each cycle is 1-7 days, preferably, 2-5 days.

It should be understood that, within the scope of the present invention, each technical feature of the present invention described above and in the following (as examples) may be combined with each other to form a new or preferred technical solution, which is not listed here due to space limitations.

DETAILED DESCRIPTION

After a long and intensive study, the inventors have synthesized a series of UTLOH compounds. The compounds of the present invention can effectively inhibit the levels of PGE2 and NO induced by LPS, and can also effectively treat an inflammation or inflammation-related disease, gout, and/or analgesia. On this basis, the inventors complete the present invention.

The compounds of the present invention may contain one or more asymmetric centers, and therefore appear as racemates, racemic mixtures, single enantiomers, diastereoisomeric compounds and single diastereomers. The asymmetric centers that can exist depend on the nature of the various substituents on the molecule. Each such asymmetric center will independently produce two optical isomers, and all possible optical isomers and diastereomer mixtures and pure or partially pure compounds are included in the scope of the present invention. The present invention includes all isomeric forms of the compounds.

The term "room temperature" herein refers to 4-40° C., preferably 20-25° C.

Compound of the Present Invention

As used herein, "the compound of the present invention" and "the compound of Formula I" can be used interchangeably, and both refer to compounds having the structure as shown in Formula I. In addition, the term further includes salts, optical isomers, racemes, solvates (such as hydrates), and/or precursors of the compounds of Formula I,

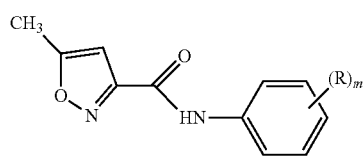
(I)

wherein, the definitions of R and m are as described above.

The preparation method of the compound of Formula I of the present invention is described in more detail below, but these specific methods do not constitute any limitation to the present invention. The compounds of the present invention can also be conveniently prepared by combining various synthetic methods described in this specification or known in the art, and such combinations can be easily performed by those skilled in the art to which the present invention belongs. Generally, in the preparation method of the present invention, each reaction is mostly carried out in an inert solvent at 0° C. to 150° C. (or reflux temperature) (preferably, 10-60° C., or 20-40° C.) for a period of time (such as 0.1-72 hours, preferably 2-20 hours).

As used herein, the room temperature refers to 4-35° C., preferably 20-30° C.

Preferably, the compound of Formula I of the present invention can be completed by the following schemes and the exemplary methods described in the examples, as well as relevant published documents used by those skilled in the art.

Typically, the preparation method of the compound of Formula I of the present invention may include (but is not limited to) the following procedures.

Scheme I (taking R is OH, m=1 as an example)

Figure 1:
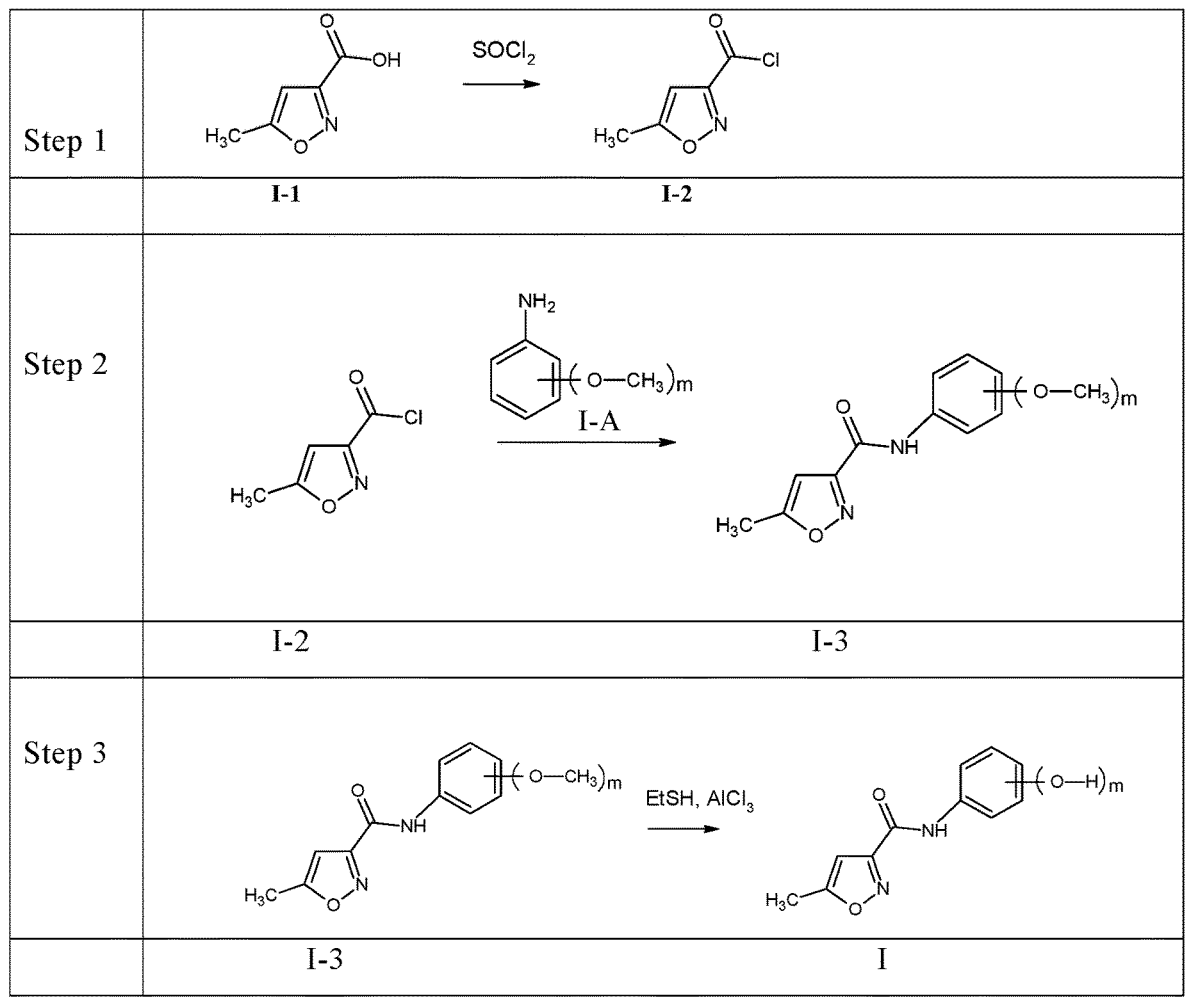
FIG. 1 shows a representative synthesis scheme of the compound of Formula I of the present invention. In short, in step 1, the starting material of 5-methylisoxazole-3-carboxylic acid (I-1) is reacted with $SOCl_2$ to prepare compound I-2. Step 2 is to prepare compound I-3 by reacting compound I-2 with compound I-A. Step 3 is to demethylate compound I-3 to prepare the compound of Formula I of the present invention.

The scheme is shown in FIG. 1. The specific scheme is as follows:

(1) Preparation of the Compound I-2

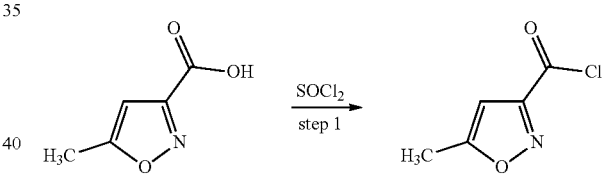

I-1 (5-methylisoxazole-3-carboxylic acid) I-2
(5-Methylisoxazole-3-carbonyl chloride)

In step 1, firstly, the compound I-1 (such as 5-methylisoxazole-3-carboxylic acid) and $SOCl_2$ are refluxed for about 1-8 hours (preferably 2-4 hours) in an inert solvent (such as dichloromethane), and the extra $SOCl_2$ is removed in vacuum, thereby forming a compound of Formula I-2.

(2) Preparation of Compound I-3

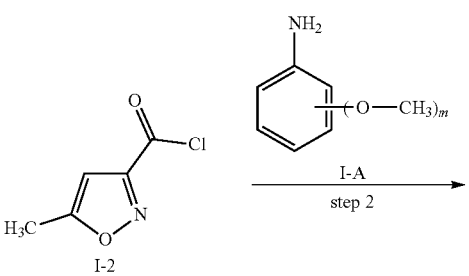

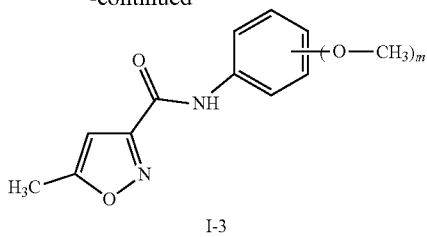

I-3

In step 2, in an inert solvent (such as dichloromethane), compound I-2 is dissolved in dichloromethane, and compound I-A (such as anisidine) is slowly added. Reaction S is carried out at room temperature, and an appropriate amount of triethylamine is added to promote the progress of the reaction. The reaction is carried out for about 0.1 hour to 4 hours (preferably 0.2 hour to 3 hours), and the dichloromethane is removed in vacuum, thereby forming a compound of Formula I-3.

(3) Preparation of Compound of Formula I

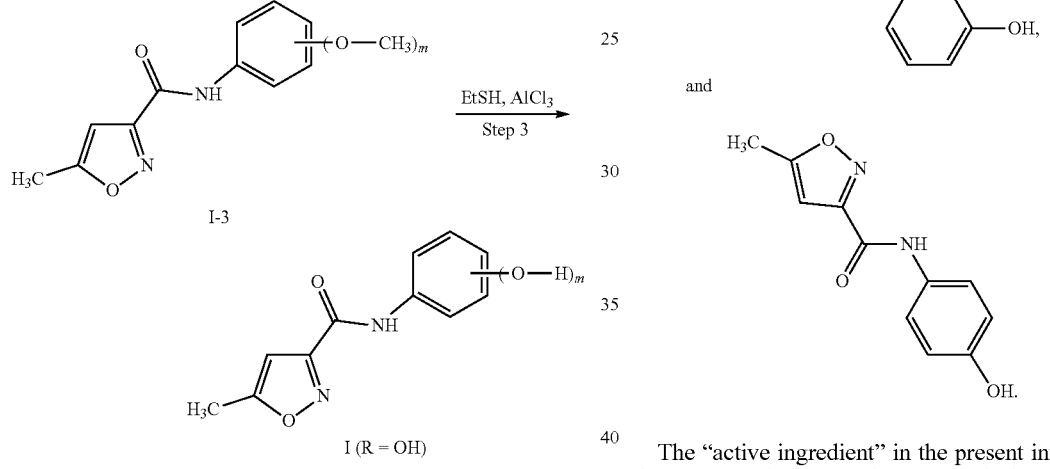

I (R = OH)

In step 3, EtSH and AlCl$_3$ are added to compound I-3 in an inert solvent (such as dichloromethane) for demethylation, thereby preparing a compound of Formula I.

Pharmaceutical Composition

The present invention also provides a pharmaceutical composition comprising
(a) an effective amount of a compound of Formula I, or a salt thereof, or an optical isomer thereof, or a raceme thereof, or a solvate thereof, or a precursor thereof and
(b) a pharmaceutically acceptable carrier.

In a preferred embodiment, the pharmaceutical composition comprises (i) a compound of Formula II, and the compound of Formula II is

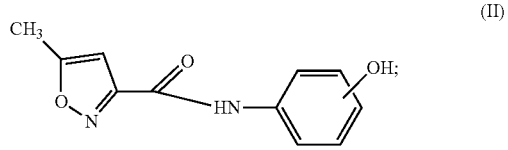

and (ii) a pharmaceutically acceptable carrier.

In a preferred embodiment, the pharmaceutical composition may further comprise (iii) an effective amount of a compound of Formula I, or a salt thereof, or an optical isomer thereof, or a raceme thereof, or a solvate thereof, or a precursor thereof.

In a preferred embodiment, the compound of Formula II is selected from the group consisting of

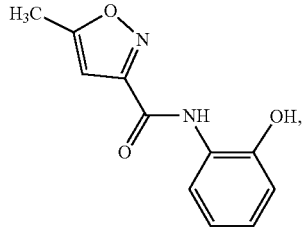

(UTLOH-4a)

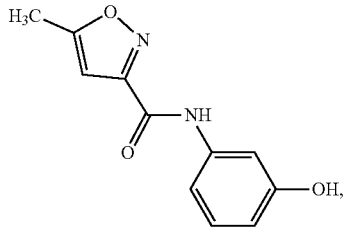

(UTLOH-4b)

and

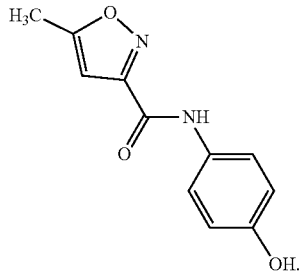

(UTLOH-4c)

The "active ingredient" in the present invention refers to the compound of Formula I, or a salt thereof, or an optical isomer thereof, or a raceme thereof, or a solvate thereof, or a precursor thereof; or the compound of Formula II.

The "active ingredients" and pharmaceutical compositions of the present invention can be used for the preparation of a medicament for (i) treating an inflammation or inflammation-related disease; and/or (ii) regulating the levels of PGE2 and NO induced by LPS; and/or (iii) treating gout; and/or (iv) analgesia.

In another preferred embodiment, the disease is selected from the group consisting of rheumatoid arthritis, osteoarthritis, psoriatic arthritis, reactive arthritis, ankylosing spondylitis, gouty arthritis, fever, mild to moderate pain caused by inflammation and tissue damage, lumbago, inflammation of the elbow, headache, migraine, acute gout, menstrual pain, metastatic bone pain, postoperation pain, muscle guarding, pain caused by Parkinson's disease and macular edema, acute onset arthritis, tophi formation, tophi chronic arthritis, urate nephropathy, uric acid urinary tract calculi, acute injury pain in soft tissue and joint, postoperation pain, obstetrics pain, acute herpes zoster pain, soft tissue and joint strain or degenerative pain, discgenic pain disease, neurogenic pain, trigeminal neuralgia, postherpetic neuralgia, intervertebral disc herniation, advanced tumor pain, tumor metastasis pain, thromboangiitis, intractable angina pectoris, idiopathic chest and abdominal pain, and a combination thereof.

"Safe and effective amount" refers to the amount of the active ingredient is sufficient to significantly improve the condition without causing serious side effects. Generally, the pharmaceutical composition contains 1-2000 mg of active ingredient/dose, and more preferably, 10-200 mg of active ingredient/dose. Preferably, the "one dose" is a tablet.

"Pharmaceutically acceptable carrier" refers to one or more compatible solid or liquid fillers or gel substances, which are suitable for human use, and must have sufficient purity and sufficiently low toxicity. "Compatibility" here means that each component in the composition can be blended with the active ingredients of the present invention and between them without significantly reducing the efficacy of the active ingredients.

The compounds of preferred embodiments of the present invention can be administered as a single active agent, or can be used in combination with one or more other agents for the treatment of inflammation or inflammation-related diseases. The compounds of the preferred embodiments of the present invention are also effective in combination with known therapeutic agents. The combination of currently known compounds and other therapeutic agents for the treatment of inflammation or inflammation-related diseases is within the scope of the preferred embodiments. Based on the specific properties of the drugs and the diseases involved, those of ordinary skill in the art can identify effective drug combinations. Such therapeutic agents for the treatment of inflammation or inflammation-related diseases include (but are not limited to) the following: dexamethasone, ibuprofen, leflunomide, teriflunomide, malononitrilamide, diclofenac sodium, diclofenac potassium, naproxen, naproxen sodium, etc. The compound of the preferred embodiment is also effective when administered simultaneously with a therapeutic agent for the treatment of inflammation or inflammation-related diseases.

The pharmaceutical composition of the present invention can be advantageously administered in the form of an injectable composition, or as a liquid solution or suspension. The additional composition is suitable for oral administration (for example, enteric-coated tablets). The oral pharmaceutical composition includes typical excipients, such as pharmaceutical grades of mannitol, lactose, starch, magnesium stearate, saccharin sodium, cellulose, magnesium carbonate and the like. The formulation of the pharmaceutical composition takes the form of solution, suspension, tablet, pill, capsule, sustained-release component or powder. When applied topically, it may be in the form of cream, factice, ointment or spray.

Generally, the compounds of the preferred embodiments will be administered in a therapeutically effective amount through any acceptable mode of agents with similar effects. The actual dosage of the compound (i.e., active ingredient) of the preferred embodiment is determined based on multiple factors, such as the severity of the disease to be treated, the age and relative health of the patient, the potency of the compound used, the route and form of administration, and other factors. The drug can be administered multiple times a day, preferably, once or twice a day. All these factors are within the consideration of the attending doctor.

In the present invention, the therapeutically effective dose can usually be a total daily dose administered to the patient at one time or in divided doses, for example, about 0.01 to about 1000 mg/kg body weight per day, preferably, about 0.1 to about 100 mg/kg body weight per day, more preferably, 1-50 mg/kg body weight. Dosage unit composition may include its dose factor to form a daily dose. The choice of dosage form depends on various factors, such as the mode of administration and the bioavailability of the drug substance. Generally, the compounds of the preferred embodiments can be administered as pharmaceutical compositions by any of the following routes: oral, systemic administration (such as transdermal, intranasal or via suppository), or parenteral administration (such as intramuscular, intravenous or subcutaneous). The preferred mode of administration is oral, and the convenient daily dose can be adjusted according to the degree of bitterness. The composition may take the form of tablets, pills, capsules, semi-solids, powders, sustained-release preparations, solutions, suspensions, elixirs, aerosols or any other suitable composition. Another preferred mode of administering the compounds of the preferred embodiments is inhalation. This is an effective method of delivering therapeutic agents directly to the respiratory tract (see, for example, U.S. Pat. No. 5,607,915).

Suitable pharmaceutically acceptable carriers or excipients include: for example, treatment agents and drug delivery modifiers and promoters, such as calcium phosphate, magnesium stearate, talc, monosaccharide, disaccharide, starch, gelatin, cellulose, sodium methyl cellulose, carboxymethyl cellulose, glucose, hydroxypropyl-β-cyclodextrin, polyvinylpyrrolidone, low melt point wax, ion exchange resin, etc., and combinations of any two or more thereof. Liquid and semi-solid excipients can be selected from glycerin, propylene glycol, water, ethanol and various oils, including petroleum, animal oil, vegetable oil or synthetic sources, such as peanut oil, soybean oil, mineral oil, sesame oil, and the like. Preferred liquid carriers, especially carriers for injectable solutions, include water, saline, glucose aqueous solution and ethylene glycol. Other suitable pharmaceutically acceptable excipients are described in "Remington's Pharmaceutical Sciences", Mack Pub. Co., New Jersey (1991), incorporated herein by reference.

As used herein, the term "pharmaceutically acceptable salt" refers to a non-toxic acid or alkaline-earth metal salt of the compound of Formula I. These salts can be prepared in situ during the final separation and purification of the compound of Formula I, or prepared by reacting a suitable organic or inorganic acid or base with a basic or acidic functional group, respectively. Representative salts include, but are not limited to acetate, adipate, alginate, citrate, aspartate, benzoate, benzene sulfonate, bisulfate, butyrate, camphorate, camphosulfonate, digluconate, cyclopentane propionate, lauryl sulfate, ethane sulfonate, glucose enanthate, glycerophosphate, hemisulphate, enanthate, caproate, fumarate, hydrochloride, hydrobromide, hydroiodide, 2-hydroxyethanesulfonate, lactate, maleate, mesylate, nicotinate, 2-naphthyl sulfonate, oxalate, pamoate, pectinate, thiocyanate, 3-phenylpropionate, picrate, pivalate, propionate, succinate, sulfate, tartrate, thiocyanate, p-toluenesulfonate and undecanoate. In addition, nitrogen-containing basic groups can be quaternized with the following reagents: alkyl halides, such as chloride, bromide and iodide of methyl, ethyl, propyl, butyl; dialkyl sulfate, such as dimethyl, diethyl, dibutyl and dipentyl sulfate; long chain halides such as chloride, bromide and iodide of decyl, lauryl, myristyl and stearyl; aralkyl halides such as benzyl and phenethyl bromide, resulting in a water-soluble or oil-soluble or dispersible product. Examples of acids that can be used to form pharmaceutically acceptable acid addition salts include inorganic acids such as hydrochloric acid, sulfuric acid, and phosphoric acid, and organic acids such as oxalic acid, maleic acid, methanesulfonic acid, succinic acid, and citric acid. The base addition salts can be prepared in situ during the final separation and purification of the compound of Formula I, or the carboxylic acid moiety is prepared by reacting with a suitable base (such as pharmaceutically acceptable hydroxides, carbonates or bicarbonates of metal cations) or ammonia, or organic primary, secondary or tertiary amines. Pharmaceutically acceptable salts include, but are not limited to, alkali metal and alkaline earth metal-based cations, such as sodium, lithium, potassium, calcium, magnesium, aluminum salts, etc., and non-toxic ammonium, quaternary ammonium and amine cations including, but not limited to ammonium, tetramethylammonium, tetraethylammonium, methylamine, dimethylamine, trimethylamine, triethylamine, ethylamine, etc. Other representative organic amines used to form base addition salts include diethylamine, ethylenediamine, ethanolamine, diethanolamine, piperazine, and the like.

As used herein, the term "pharmaceutically acceptable prodrug" refers to those prodrugs of the compounds of the preferred embodiments, which are rapidly converted into the parent compound represented by the above general formulas in vivo, for example, hydrolyzed in blood. In "T. Higuchi and V. Stella, Pro-drugs as Novel Delivery Systems, volume 14 of A.C.S. 15 Symposium Series" and "edited by Edward B. Roche, Bioreversible Carriers in Drug Design, American Pharmaceutical Association and Pergamon Press, 1987", a complete discussion is provided, both of which are incorporated herein by reference.

Uses of the Compounds of the Present Invention

The present invention also provides the use of the compound of Formula I.

The present invention also provides the use of a pharmaceutical composition containing the compound of Formula I of the present invention or a pharmaceutical composition containing the compound of Formula II of the present invention or a pharmaceutical composition containing the compound of Formula I and Formula II of the present invention.

In a preferred embodiment of the present invention, the compound of Formula I is used for manufacturing a medicament or a preparation for (i) treating inflammation or inflammation-related diseases; and/or (ii) regulating the levels of PGE2 and NO induced by LPS.

In a preferred embodiment of the present invention, the pharmaceutical composition containing the compound of Formula I of the present invention or the pharmaceutical composition containing the compound of Formula I and the compound of Formula II of the present invention is used to prepare a medicament or a preparation, and the medicament or preparation is used to (i) treat inflammation or inflammation-related diseases; and/or (ii) regulate the levels of PGE2 and NO induced by LPS; and/or (iii) treat gout; and/or (iv) analgesia.

In a preferred embodiment of the present invention, the disease is selected from the group consisting of rheumatoid arthritis, osteoarthritis, psoriatic arthritis, reactive arthritis, ankylosing spondylitis, gouty arthritis, fever, mild to moderate pain caused by inflammation and tissue damage, lumbago, inflammation of the elbow, headache, migraine, acute gout, menstrual pain, metastatic bone pain, postoperation pain, muscle guarding, pain caused by Parkinson's disease and macular edema, acute onset arthritis, tophi formation, tophi chronic arthritis, urate nephropathy, uric acid tract calculi, acute injury pain in soft tissue and joint, postoperation pain, obstetrics pain, acute herpes zoster pain, soft tissue and joint strain or degenerative pain, discgenic pain disease, neurogenic pain, trigeminal neuralgia, postherpetic neuralgia, intervertebral disc herniation, advanced tumor pain, tumor metastasis pain, thromboangiitis, intractable angina pectoris, idiopathic chest and abdominal pain, and a combination thereof.

The compound of the present invention has very good druggability (such as solubility, bioavailability, etc.).

PGE2 Regulation

Prostaglandins (PGs) play an important role in the production of inflammation. A significant increase in their biosynthesis in inflamed tissues contributes to the development of the main signs of acute inflammation: redness, heat, swelling and pain. Prostaglandin E2 (PGE2) is one of the most abundant prostaglandins (PGs) produced in the body, and it is also an important mediator of many biological functions. PGE2 is of particular interest to inflammation because it involves all processes that lead to the classic signs of inflammation: redness, swelling and pain.

In the present invention, the compound of the present invention can modulate the level of PGE2 induced by LPS.

In a preferred embodiment, the compound of the present invention has an inhibitory effect on the level of PGE2 induced by LPS.

NO Regulation

Nitric oxide (NO) is a signaling molecule that plays a key role in the pathogenesis of inflammation. Under abnormal conditions, NO is a pro-inflammatory mediator that causes inflammation due to its overproduction. Therefore, the regulation of elevated NO levels by stimulants (such as LPS) has been widely used as a screening method to identify anti-inflammatory drugs. Since NO is oxidized into nitrite and nitrate, the determination of total $NO_2^-/NO_3^-$ is a conventional method for determining NO levels, and Griess reagent is usually used in this type of experiment.

In the present invention, the compounds of the present invention can regulate the level of NO induced by LPS.

In a preferred embodiment, the compound of the present invention has an inhibitory effect on the level of NO induced by LPS.

The Main Advantages of the Present Invention Include:

(1) Providing compound of Formula I with novel structure.

(2) The compound of the present invention can regulate the anti-inflammatory effects represented by PGE2 and NO.

(3) The compound of the present invention can treat inflammation or inflammation-related diseases.

(4) The synthesis method is mild, the operation is simple and easy, the yield is high, it is easy to derivatize, and it is suitable for industrial scale-up production.

(5) The compound of the present invention has very good druggability (such as solubility, bioavailability, etc.).

(6) The compound of the present invention can increase water solubility and bioavailability. In addition, the increased solubility makes the preparation of dosage forms easier.

(7) The compound of Formula I of the present invention can be used alone or in combination with the compound of Formula II to treat inflammation or inflammation-related diseases, and to regulate the anti-inflammatory effects represented by PGE2 and NO.

Unless otherwise defined, all professional and scientific terms used herein have the same meaning as those familiar to those skilled in the art. In addition, any method and material similar or equal to the content described can be applied to the method of the present invention. The preferred embodiments and materials described herein are for demonstration purposes only.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (New York: Cold Spring Harbor Laboratory Press, 1989) or as instructed by the manufacturer. Unless otherwise specified, all percentages, or parts are by weight.

Unless otherwise specified, the reagents and materials used in the examples of the present invention are all commercially available products.

Figure 2:
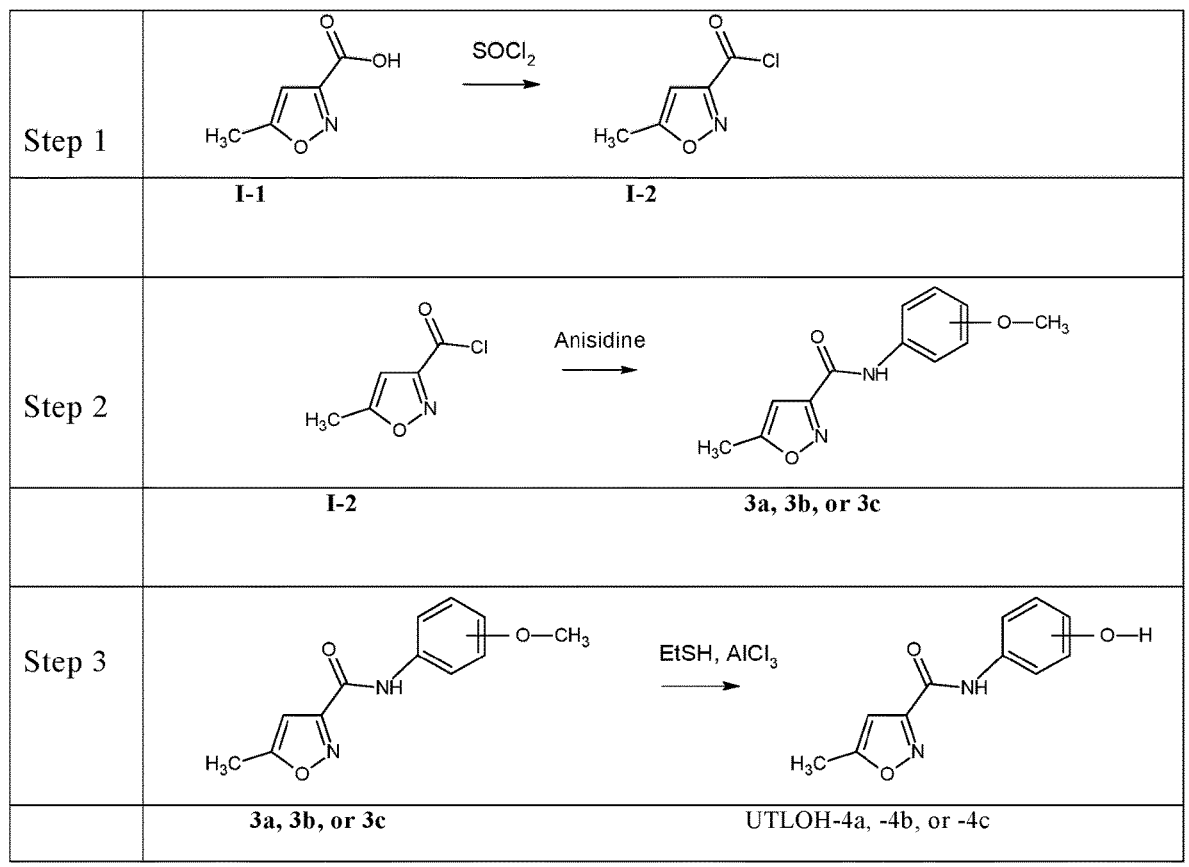
FIG. 2 shows a representative synthesis scheme of UTLOH compound (i.e., UTLOH-4a, -4b, and -4c). In short, in step 1, the starting material of 5-methylisoxazole-3-carboxylic acid (I-1) is reacted with $SOCl_2$ to prepare compound I-2. Step 2 is to prepare compound 3a, 3b or 3c by reacting compound I-2 with corresponding anisidine (such as o-, m-, or p-anisidine). Step 3 is to demethylate compound 3a, 3b or 3c to prepare UTLOH-4a, -4b or -4c.

Example 1 Representative Synthesis Schemes, Procedures and Results of Three UTLOH Compounds The synthesis of UTLOH series compounds can be illustrated by the representative examples as shown in FIG. 2. FIG. 2 shows the synthesis scheme of UTLOH-4a, -4b and -4c. Using the corresponding di-methoxyaniline or tris-methoxyaniline instead of anisidine, and using the same procedure to synthesize other UTLOH compounds.

The steps to synthesize UTLOH-4a, -4b, and -4c can be described below. Briefly, the starting material (5-methyl-isoxazole-3-carboxylic acid) (1.27 g, 10 mmol) in 30 mL of dichloromethane was refluxed for 3 hours with thionyl chloride (10 mL). Excess thionyl chloride was removed in vacuo to obtain compound 2. Anisidine (o-, m- or p-anisidine) (1.23 g, 10 mmol) was slowly added to compound 2 in 10 ml of dichloromethane. Then 5 ml of triethylamine in dichloromethane was added to the mixture. The mixture was then stirred for 30 minutes and the dichloromethane was removed in vacuo. Diluted HCl was added and the crude product was extracted 3 times with ethyl acetate. The organic layers were combined, dried with $Na_2SO_4$, filtered, and then recrystallized to obtain compound 3a, 3b or 3c.

| Compound | OCH$_3$ position | Yield (%) | appearance |
| --- | --- | --- | --- |
| 3a | ortho-position | 92 | white |
| 3b | meta-position | 89 | white |
| 3c | para-position | 93 | white |

Ethanethiol (1.55 g, 25 mmol) and $AlCl_3$ (4.99 g, 37.5 mmol) were added to compound 3a, 3b or 3c (1.16 g, 5 mmol) in dichloromethane (30 mL), and stirred at room temperature for 20 minutes, then ice-water was poured to precipitate the crude product. After filtration, the precipitate was washed with water until it is acid-free. The crude product was recrystallized in dichloromethane to obtain compound UTLOH-4a, -4b or -4c.

| Compound | OH position | Yield (%) | appearance |
| --- | --- | --- | --- |
| UTLOH-4a | ortho-position | 77 | white |
| UTLOH-4b | meta-position | 80 | white |
| UTLOH-4c | para-position | 82 | white |

Example 2 UTLOH Compound of the Present Invention Regulates PGE2 and NO Induced by LPS This example is taken from a previous publication by Song et al.[1]. In brief, mice RAW 264.7 cells were treated with increasing doses of each test compound at 37° C. for 1 hour. Thereafter, the cells were attacked with 20 μL/well of LPS (equivalent to a final concentration of 100 ng/mL). The cells were further incubated overnight at 37° C. A commercial ELISA assay kit obtained from R&D Systems (Minneapolis, Minn.) was used to determine the level of PGE2 in the supernatant, and three parallel experiments were performed. The optical density of each well was measured using a BioTek Epoch microplate reader (Winooski, Vt.) set to 450 nm. The NO study was performed in a similar manner, but Greiss reagent was used to monitor the level of NO, and the results were read at 550 nm. The results are shown in Table 1:

TABLE 1

Inhibition results of PGE2 and NO induced by LPS

| Compound | PGE2 inhibition (%) | NO IC$_{50}$ (μM)* (+: >250; ++: 150-250; +++: 50-150; ++++: 10-50; +++++: <10) |
| --- | --- | --- |
| Leflunomide | 54.0 | + (298) |
| Teriflunomide | 70.2 | ++ (175) |
| UTLOH-4a | 98.5 | +++++ (1.4) |
| UTLOH-4b | 64.0 | +++++ (7.7) |
| UTLOH-4c | 73.1 | +++++ (6.3) |

*By adding test compounds at a concentration of up to 200 μM, MTT assay is used to show that the cell growth of all LPS-activated mice RAW 264.7 macrophages has no significant effect (cell viability ≥85%).

Studies have shown that, compared to leflunomide, the compounds of the present invention (such as UTLOH-4a and UTLOH-4c) have stronger inhibition on PGE2; the inhibition of LPS-induced NO shows that the compounds of the present invention (such as UTLOH-4a and UTLOH-4c) inhibits NO more strongly than leflunomide and teriflunomide (the active metabolite of leflunomide).

In addition, other compounds of the present invention (such as UTLOH-4d, UTLOH-4e, UTLOH-4f, UTLOH-4g, UTLOH-4h, UTLOH-4i, UTLOH-4k) were measured using the same experimental method of the present invention, and the experiment shows that other compounds of the present invention (such as UTLOH-4d, UTLOH-4e, UTLOH-4f, UTLOH-4g, UTLOH-4h, UTLOH-4i, UTLOH-4k) have very good PGE2 inhibition rate, and the IC$_{50}$ of NO is at 10-50 μM, or at the range of <10 μM, similar to UTLOH-4a, UTLOH-4b and UTLOH-4c.

Based on these results, it can be concluded that the UTLOH series compounds of the present invention have very significant anti-inflammatory activity.

Example 3 The Effect of UTLOH Compound of the Present Invention on Hot Plate Pain in Mice The hot plate method uses a certain intensity of warm heat to stimulate mice to produce pain reaction. This experiment observes the analgesic effect of UTLOH series compounds. Female SPF-grade Kunming mice (18-22 g/mouse) were put in a hot plate apparatus at a temperature of 55±0.5° C., and the pain threshold of the mice was measured. The measurement was performed twice, and the measurement was performed every 5 minutes. Taking the mouse licking hind feet as the observation index. The mice with pain response within 30 s were selected as experimental animals. The pre-selected qualified mice were randomly grouped according to their body weight. The blank group was intraperitoneally injected with 0.2 ml/10 g body weight of normal saline, and the other groups were intraperitoneally injected with corresponding drugs. The pain threshold was measured 30 and 60 minutes after the administration. If the mouse had no pain within 60 seconds, it was taken out immediately and calculated at 60 seconds.

It can be seen from Table 2 that the two doses of 100 mg/kg and 200 mg/kg of compound UTLOH-4a can significantly reduce the percentage increase in the pain threshold of the mouse hot plate experiment at 30 and 60 minutes after administration. The 25 mg/kg and 200 mg/kg dose groups of UTLOH-4e can significantly reduce the percentage increase in the pain threshold of mice 30 minutes after administration.

TABLE 2

Effects of UTLOH series compounds on the pain threshold of the hot plate experiment in mice ($\bar{x} \pm s$)

| Group | Dosage (mg/kg) | N | Percentage increase in pain threshold (%) 30 min | 60 min |
|---|---|---|---|---|
| normal group | — | 11 | 12.68 ± 26.98 | −3.66 ± 28.39 |
| UTLOH-4a | 25 | 10 | −15.08 ± 37.87 | −16.76 ± 33.81 |
| UTLOH-4a | 50 | 9 | −6.95 ± 41.45 | −32.96 ± 35,54 |
| UTLOH-4a | 100 | 11 | −19.99 ± 38.23* | −34.23 ± 39.23* |
| UTLOH-4a | 200 | 10 | −30.12 ± 27.69** | −29.65 ± 24.62* |
| UTLOH-4e | 25 | 10 | −17.71 ± 38.50* | −2.76 ± 34.01 |
| UTLOH-4e | 50 | 10 | −3.15 ± 46.73 | 8.36 ± 84.14 |
| UTLOH-4e | 100 | 10 | 15.50 ± 103.74 | −11.18 ± 85.76 |
| UTLOH-4e | 200 | 10 | −28.73 ± 28.36** | −16.72 ± 40.12 |

Note:
All data are expressed as mean ± standard deviation ($\bar{x} \pm s$).
Compared with the normal group,
*P < 0.05,
**P < 0.01.

Example 4 The Effect of the UTLOH Compound of the Present Invention on the Writhing Response of Mice Induced by Intraperitoneal Injection of Glacial Acetic Acid After glacial acetic acid is injected into the abdominal cavity of mice, it can cause inflammatory pain and cause writhing reaction in mice. In this experiment, the analgesic effects of UTLOH compounds were observed by the number of writhing times in mice after intraperitoneal injection of glacial acetic acid.

Taking 100 KM mice, SPF grade, half male and half male (18-22 g/mouse), and randomly grouping them according to their body weight. Except that the blank control group was given 0.5% CMC-Na suspension by gavage administration, the other groups were given the corresponding drugs by gavage for 3 continuous days, once a day, with a gavage volume of 0.2 ml/10 g. 30 minutes after the administration on the 3rd day, each group of mice was intraperitoneally injected with 0.6% glacial acetic acid, 0.1 ml/10 g, to create writhing reaction model in mice. The number of writhing times of mice in each group within 15 minutes after 5 minutes injection of glacial acetic acid was observed and the inhibition rate was calculated.

It can be seen from Table 3 that the four dose groups of UTLOH-4a and UTLOH-4e can significantly inhibit the writhing response in mice induced by acetic acid.

TABLE 3

Analgesic effects of UTLOH series compounds on writhing response of mice with acetic acid ($\bar{x} \pm s$)

| Group | Dosage (mg/kg) | N | Writhing reaction inhibition percentage (%) |
|---|---|---|---|
| Normal group | — | 11 | −0.01 ± 13.79 |
| UTLOH-4a | 25 | 11 | 21.63 ± 29.24* |
| UTLOH-4a | 50 | 12 | 24.26 ± 10.11** |
| UTLOH-4a | 100 | 12 | 28.48 ± 15.74** |
| UTLOH-4a | 200 | 11 | 23.05 ± 10.08** |
| UTLOH-4e | 25 | 11 | 36.52 ± 10.08** |
| UTLOH-4e | 50 | 11 | 35.63 ± 17.03** |
| UTLOH-4e | 100 | 11 | 39.54 ± 15.18** |
| UTLOH-4e | 200 | 11 | 30.14 ± 17.18** |

Note:
All data are expressed as mean ± standard deviation ($\bar{x} \pm s$).
Compared with the normal group,
*P < 0.05,
**P < 0.01.

Example 5 Effect of UTLOH Compound of the Present Invention on Xylene-Induced Ear Swelling in Mice Xylene applied to the ears of mice can cause acute inflammatory swelling of the ears of the mice. The anti-inflammatory effects of the tested drugs were observed by the degree of swelling of the ears of the mice after the inflammation.

Taking Kunming mice, SPF grade, half male and half male (18-22 g/mouse) and randomly grouping them according to body weight. The normal control group was given 0.5% CMC-Na suspension by gavage administration, and the other groups were given corresponding drugs (0.2 ml/10 g) for 3 consecutive days, once a day. 0.5 h after the last administration, 0.02 ml of xylene was applied to the right auricle of each group of mice, and the left side was not applied as a control, establishing a mouse ear swelling model. 20 minutes after the inflammation, the mice were killed by cervical dislocation. Both ears were cut along the baseline of the auricle, and the discs on the same part of the left and right ears were punched out with a punch (6 mm of diameter) and weighed.

As shown in Table 4, the ear swelling rate of the three dose groups of UTLOH-4a and -4e on mice is significantly lower than that of the normal group, and UTLOH-4e shows good dose-dependent, the higher the dose, the lower the ear swelling rate of mice.

TABLE 4

Effects of UTLOH series compounds on xylene-induced ear swelling in mice ($\bar{x} \pm s$)

| Group | Dosage (mg/kg) | N | Swelling rate (%) |
|---|---|---|---|
| Normal group | — | 11 | 77.37 ± 24.56 |
| UTLOH-4a | 6.25 | 10 | 49.77 ± 22.15* |
| UTLOH-4a | 12.5 | 10 | 50.59 ± 21.52* |
| UTLOH-4a | 25 | 10 | 49.87 ± 16.44** |
| UTLOH-4e | 6.25 | 10 | 53.22 ± 28.01* |
| UTLOH-4e | 12.5 | 10 | 42.98 ± 23.60** |
| UTLOH-4e | 25 | 10 | 41.29 ± 21.75** |

Note:
All data are expressed as mean ± standard deviation ($\bar{x} \pm s$).
Compared with the normal group,
*P < 0.05,
**P < 0.01.

Example 6 The Effect of UTLOH Compound of the Present Invention on Rat Paw Swelling Caused by Egg White Injecting 10% egg white into rat paws can cause early acute inflammation such as redness, heat, swelling, and pain in rat paws. In this experiment, the anti-inflammatory effects of UTLOH series compounds were observed by the degree of swelling of the paws of rats after inflammation.

SPF grade SD rats, half female and half male (100-120 g/mouse) were randomly grouped according to body weight. Each group was given the corresponding drugs by gavage, once a day, for 3 consecutive days, with a gavage volume of 1 ml/100 g. Before the experiment, the ankle joint of the right hind foot of each group of rats was marked, and the foot volume of each group of rats was measured twice with a rat foot volume meter, and the average of the two times was taken as the inflamed forefoot volume. 30 minutes after the last administration, the rats in each group were given a subcutaneous needle in the right hind paw, and injected with 10% fresh egg white solution 0.1 ml/mouse to cause inflammation, establishing a rat model of paw swelling. The post-inflamed foot volume in mice was measured twice at 1 h, 2 h, 3 h, and 4 h after inflammation, and the average of the two times was taken as the post-inflamed foot volume. The normal group was given 1 ml/100 g volume of 0.5% CMC-Na solution by gavage according to body weight.

As shown in Table 5, compared with the normal group, the degree of foot swelling in the leflunomide group is significantly reduced at 1 h and 2 h. UTLOH-4a low-, medium-, and high-dose group can significantly reduce foot swelling at 1 h after inflammation. The foot swelling degree of the UTLOH-4e low-dose group is significantly reduced at 1 h after inflammation, and the foot swelling degree of the medium-dose group and high-dose group are significantly reduced at 1 h, 2 h, and 3 h after inflammation.

and centrifuged. Operated according to the kit instructions to determine the blood uric acid (UA) level in each group of mice; determine the xanthine oxidase (XOD) activity in the supernatant of mouse liver homogenate.

As shown in Table 6-1, intraperitoneal injection of 300 mg/kg oxonic acid potassium salt in mice can cause acute hyperuricemia. Compared with the normal group, the uric acid in the serum of the mice in the model group was increased significantly. UTLOH-4e can significantly reduce the level of uric acid in the serum of model mice.

Intraperitoneal injection of oxonic acid potassium salt can increase the activity of xanthine oxidase (XOD) in the liver of mice. As shown in Table 6-2, compared with the normal group, the XOD activity of the liver in the mice of the model group is increased significantly. UTLOH-4e can significantly reduce the liver XOD activity of model mice.

TABLE 5

Effects of UTLOH series compounds on 10% egg white-induced foot swelling in rats ($\bar{x} \pm s$, n = 10)

| Group | Dosage (mg/kg) | Foot swelling (ml) | | | |
|---|---|---|---|---|---|
| | | 1 h | 2 h | 3 h | 4 h |
| Normal group | — | 0.82 ± 0.15 | 0.75 ± 0.12 | 0.62 ± 0.08 | 0.43 ± 0.09 |
| Leflunomide group | 6.67 | 0.63 ± 0.14** | 0.62 ± 0.15* | 0.54 ± 0.14 | 0.43 ± 0.11 |
| UTLOH-4a | 10 | 0.50 ± 0.08** | 0.79 ± 0.07 | 0.63 ± 0.13 | 0.47 ± 0.13 |
| UTLOH-4a | 20 | 0.55 ± 0.11** | 0.79 ± 0.14 | 0.64 ± 0.15 | 0.48 ± 0.12 |
| UTLOH-4a | 40 | 0.65 ± 0.18* | 0.77 ± 0.11 | 0.57 ± 0.15 | 0.48 ± 0.12 |
| UTLOH-4e | 10 | 0.67 ± 0.15* | 0.66 ± 0.15 | 0.60 ± 0.16 | 0.44 ± 0.07 |
| UTLOH-4e | 20 | 0.69 ± 0.08* | 0.55 ± 0.13** | 0.51 ± 0.09* | 0.38 ± 0.12 |
| UTLOH-4e | 40 | 0.69 ± 0.13* | 0.57 ± 0.17* | 0.49 ± 0.15* | 0.45 ± 0.16 |

Note:
All data are expressed as mean ± standard deviation.
Compared with the normal group,
*P < 0.05,
**P < 0.01.
a: UTLOH-4a, e: UTLOH-4e.

Example 7 The Effect of the UTLOH Compound of the Present Invention on the Hyperuricemia Model Mice Induced by Oxonic Acid Potassium Salt Oxoxazine potassium salt can directly increase blood uric acid levels in animals. In this experiment, intraperitoneal injection of oxonic acid potassium salt was used to observe the uric acid-lowering effect of UTLOH series drugs.

SPF grade KM mice, half female and half male (18-22 g/mouse). After the animals were adaptively fed for 3 days, they were randomly grouped by body weight. It was administered once a day for 7 consecutive days by gavage. On the 7th day, 1 hour before the gavage administration, the mice were intraperitoneally injected with a dose of 300 mg/kg of oxonic acid potassium salt. After the administration, the eyeballs were removed to take blood, and the serum was separated for testing. After decapitation, the liver was taken, weighed, cut into pieces, added with saline, homogenized,

TABLE 6-1

Effects of UTLOH series compounds on serum UA levels in OA-induced hyperuricemia model mice ($\bar{x} \pm s$)

| Group | Dosage (mg/kg) | n | UA (μmol/l) |
|---|---|---|---|
| Normal group | — | 10 | 39.61 ± 12.14 |
| Model group | — | 10 | 67.86 ± 11.83## |

TABLE 6-1-continued

Effects of UTLOH series compounds on serum UA levels in OA-induced hyperuricemia model mice ($\bar{x} \pm s$)

| Group | Dosage (mg/kg) | n | UA (μmol/l) |
|---|---|---|---|
| UTLOH-4e | 6.25 | 10 | 50.07 ± 9.86** |
| UTLOH-4e | 12.5 | 11 | 47.15 ± 13.48** |

Note:
All data are expressed as mean ± standard deviation.
Compared with the normal group,
P < 0.05,
P < 0.01.
Compared with the model group,
*P < 0.05,
**P < 0.01.

TABLE 6-2

Effect of UTLOH series compounds on XOD activity of liver in OA-induced hyperuricemia model mice ($\bar{x} \pm s$)

| Group | Dosage (mg/kg) | N | XOD(U/gprot) |
|---|---|---|---|
| Normal group | — | 10 | 22.65 ± 2.86 |
| Model group | — | 10 | 28.04 ± 4.65## |
| UTLOH-4e | 6.25 | 10 | 21.55 ± 2.00** |
| UTLOH-4e | 12.5 | 11 | 22.54 ± 3.98** |

Note:
All data are expressed as mean ± standard deviation. Compared with the normal group, #P < 0.05, ##P < 0.01. Compared with the model group, *P < 0.05, **P < 0.01. XOD in the table is calculated according to the following formula:

$$XOD(U/gprot) = \frac{\text{measured } OD \text{ value} - \text{blanc } OD \text{ value}}{\text{molar extinction coefficient of colored matter}} \times \frac{\text{total volume of reaction solution}}{\text{sampling volume} \times \text{colorimetric light diameter} \times \text{reaction time}} + \text{protein concentration of sample to be tested } (gprot/L).$$

Example 8 The Effect of UTLOH Compound of the Present Invention on Acute Gouty Arthritis in Rats Induced by Sodium Urate Crystals Injecting sodium urate crystals into the joint cavity to establish an acute gouty arthritis model. Its pathological and clinical manifestations are very similar. It is a classic method commonly used in animal experiments to study gouty arthritis. This experiment will explore the effects of UTLOH series drugs on animals with acute gouty arthritis induced by sodium urate.

SPF grade SD rats, half female and half male (200-220 g/mouse), were randomly grouped by weight. The drug was administered once a day, for 3 consecutive days. After 1 hour of administration on the third day, slightly improved according to classic methods such as Coderre, that is, a 1 ml injection needle was inserted into the inner side of the tibial tendon at 45 degrees on the dorsal side of the right ankle joint of the tested rat, and 0.2 ml of 2.5 g/100 ml sodium urate solution was injected into the ankle joint cavity, resulting in a model of acute gouty arthritis lesion. Rats in the normal group were injected with an equal volume of sterile saline to the back of the right ankle joint. The administration was continued after modeling, once a day for 3 consecutive days. The ankle joint and foot volume of the rats in each group were measured respectively before modeling and 2 h, 4 h, 8 h, 24 h and 48 h after modeling.

As shown in Table 7, after sodium urate crystals are injected into the ankle joint cavity of rats, the degree of foot swelling is significantly higher than that of the normal group injected with the same volume of normal saline. There are significant differences in the degree of foot swelling at each time point. In rats gavage administered with colchicine, the degree of foot swelling at each time point is significantly lower than that of the model group. Compared with the model group, the low-, medium- and high-dose groups of UTLOH-4a can significantly reduce foot volume at 24 h and 48 h after injection of sodium urate crystals. The medium- and high-dose groups of UTLOH-4e can significantly reduce the foot volume at 2 h, 4 h, 8 h, 24 h and 48 h after injection of sodium urate crystals. The results show that in this rat model of acute gouty arthritis, UTLOH-4e can significantly inhibit the swelling of the rat ankle joint after 2 h, and the anti-swelling effect of UTLOH-4a is reflected in 24 h after modeling.

TABLE 7

Effects of UTLOH series compounds on foot swelling in rats with acute gouty arthritis ($\bar{x} \pm s$, n = 9-10)

| Group | Dosage (mg/kg) | Foot swelling (ml) | | | | |
|---|---|---|---|---|---|---|
| | | 2 h | 4 h | 8 h | 24 h | 48 h |
| Normal group | — | 0.10 ± 0.05 | 0.13 ± 0.12 | 0.11 ± 0.14 | 0.01 ± 0.10 | −0.02 ± 0.08 |
| Model group | — | 0.36 ± 0.12## | 0.35 ± 0.10## | 0.33 ± 0.11## | 0.37 ± 0.15## | 0.20 ± 0.12## |
| Colchicine | 16.67 | 0.16 ± 0.12** | 0.21 ± 0.10** | 0.19 ± 0.10* | 0.20 ± 0.10** | 0.07 ± 0.09** |
| UTLOH-4a | 10 | 0.33 ± 0.20 | 0.31 ± 0.10 | 0.29 ± 0.09 | 0.20 ± 0.11** | 0.03 ± 0.11** |
| UTLOH-4a | 20 | 0.28 ± 0.13 | 0.3 ± 0.13 | 0.32 ± 0.09 | 0.21 ± 0.14* | 0.07 ± 13* |
| UTLOH-4a | 40 | 0.30 ± 0.13 | 0.36 ± 0.13 | 0.36 ± 0.09 | 0.19 ± 0.11** | 0.11 ± 0.09* |
| UTLOH-4e | 10 | 0.28 ± 0.09* | 0.34 ± 0.07 | 0.33 ± 0.11 | 0.22 ± 0.12** | 0.05 ± 0.07** |
| UTLOH-4e | 20 | 0.18 ± 0.07** | 0.24 ± 0.06** | 0.19 ± 0.07** | 0.19 ± 0.12** | 0.09 ± 0.08* |
| UTLOH-4e | 40 | 0.20 ± 0.08** | 0.25 ± 0.05** | 0.19 ± 0.10** | 0.22 ± 0.07** | 0.09 ± 0.12* |

Note:
All data are expressed as mean ± standard deviation ($\bar{x} \pm s$).
Compared with the normal group,
P < 0.05,
P < 0.01.
Compared with the model group,
*P < 0.05,
**P < 0.01.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

REFERENCE

1. Song, Y., et al., Comparison of two molecular scaffolds, 5-methylisoxazole-3-carboxamide and 5-methylisoxazole-4-carboxamide. Curr Pharm Des, 2014. 20(1): p. 146-52.

The invention claimed is:

1. A compound of Formula I, or a salt thereof, or an optical isomer thereof, or a raceme thereof, or a solvate thereof,

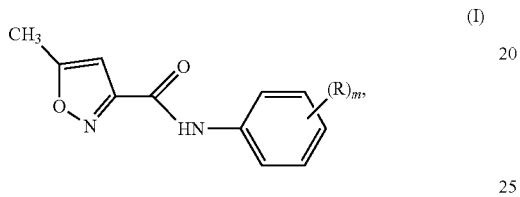

(I)

wherein each R is independently selected from the group consisting of —OH and —OCH$_2$CH$_3$; and m is an integer of 2 or 3.

2. The compound of Formula I, or a salt thereof, or an optical isomer thereof, or a raceme thereof, or a solvate thereof of claim 1, wherein the compound is selected from the group consisting of

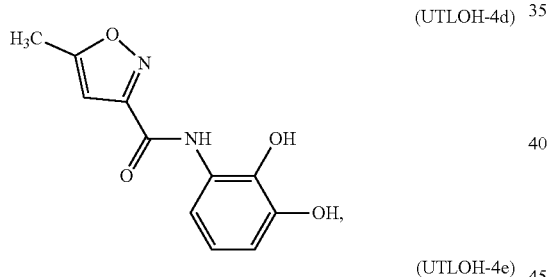

(UTLOH-4d)

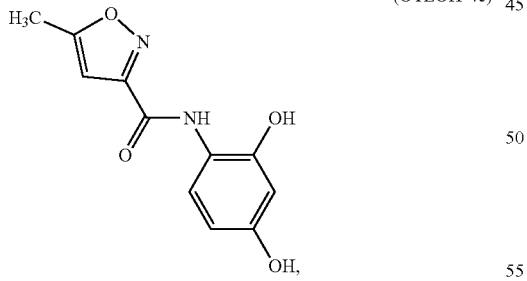

(UTLOH-4e)

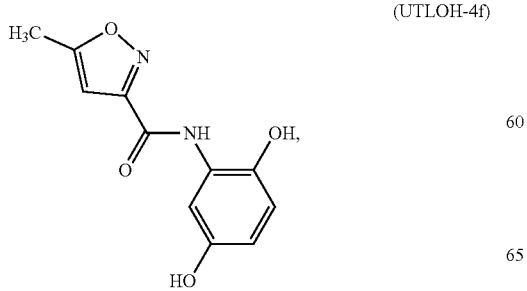

(UTLOH-4f)

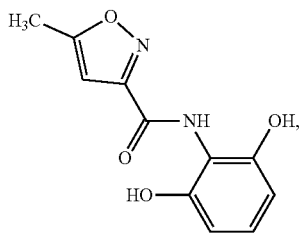

(UTLOH-4g)

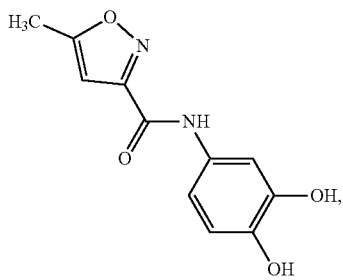

(UTLOH-4h)

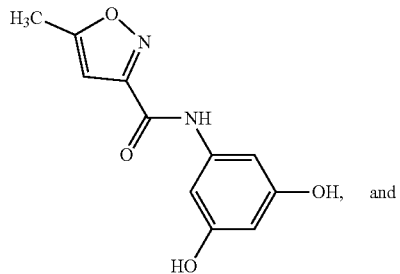

(UTLOH-4i)

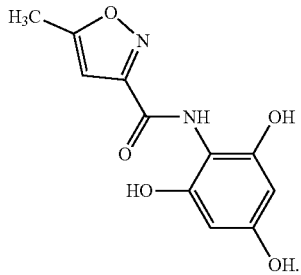

(UTLOH-4k)

3. A pharmaceutical composition, comprising:
(i) the compound of Formula I, or a salt thereof, or an optical isomer thereof, or a raceme thereof, or a solvate thereof of claim 1; and
(ii) a pharmaceutically acceptable carrier;
wherein the definition of the compound of Formula I is as described in claim 1.

4. A pharmaceutical composition, comprising:
(i) a first active ingredient, the first active ingredient is a compound of Formula II,

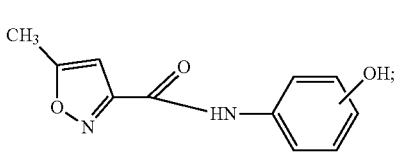

(II)

and (ii) a pharmaceutically acceptable carrier;

wherein the pharmaceutical composition further comprises a second active ingredient, which is the compound of Formula I, or a salt thereof, or an optical isomer thereof, or a raceme thereof, or a solvate thereof of claim 1; wherein the definition of the compound of Formula I is as described in claim 1.

5. The pharmaceutical composition of claim 4, wherein the compound of Formula II is selected from the group consisting of

(UTLOH-4a)

(UTLOH-4b)

and

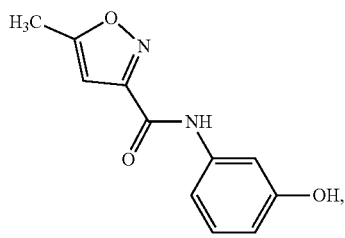
(UTLOH-4c)

6. The pharmaceutical composition of claim 4, wherein the weight ratio of the first active ingredient and the second active ingredient is 1:100 to 100:1.

7. A method for treating an inflammation or inflammation-related disease; and/or regulating the levels of PGE2 and NO induced by LPS, comprising:
    administering to a subject in need thereof the compound of Formula I, or a salt thereof, or an optical isomer thereof, or a raceme thereof, or a solvate thereof of claim 1; or
    administering to a subject in need thereof
    a pharmaceutical composition comprising:
        (i) the compound of Formula I, or a salt thereof, or an optical isomer thereof, or a raceme thereof, or a solvate thereof of claim 1; and
        (ii) a pharmaceutically acceptable carrier; or
    a pharmaceutical composition comprising:
        (i) a first active ingredient, the first active ingredient is a compound of Formula II,

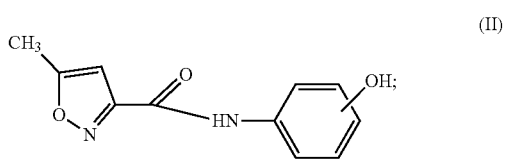
(II)

and (ii) a pharmaceutically acceptable carrier.

8. A method for preparing a compound of Formula I or a salt thereof, comprising reacting compound I-2 with compound I-A1 in an inert solvent, thereby forming a compound of Formula I;

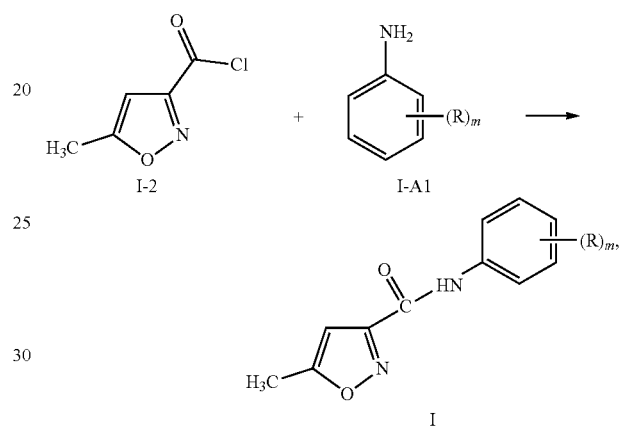

wherein in the above formulas, R and m are defined as described in claim 1.

9. An in vitro method for inhibiting PGE2 and NO induced by LPS, comprising:
    in the presence of LPS, contacting the compound of Formula I, or a salt thereof, or an optical isomer thereof, or a raceme thereof, or a solvate thereof of claim 1, or
    a compound of Formula II, or
    a pharmaceutical composition comprising:
        (i) the compound of Formula I, or a salt thereof, or an optical isomer thereof, or a raceme thereof, or a solvate thereof of claim 1; and
        (ii) a pharmaceutically acceptable carrier;
    with a mammalian cell, wherein the compound of Formula I or the compound of Formula II inhibits the levels of PGE2 and NO induced by LPS, and wherein
    the compound of Formula II is

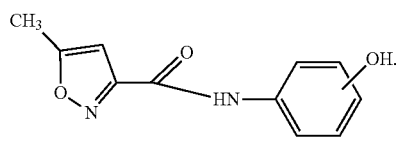

10. The pharmaceutical composition according to claim 6, wherein the weight ratio of the first active ingredient and the second active ingredient is 1:10 to 10:1.

* * * * *